United States Patent [19]

Genna

[11] Patent Number: 4,783,417
[45] Date of Patent: Nov. 8, 1988

[54] SYSTEM FOR ON-LINE MOLTEN METAL ANALYSIS

[75] Inventor: John L. Genna, Monroeville, Pa.

[73] Assignee: Aluminum Company of America, Pittsburgh, Pa.

[21] Appl. No.: 826,988

[22] Filed: Feb. 7, 1986

[51] Int. Cl.⁴ .................. G01N 1/10; G01N 21/62; G01N 33/20

[52] U.S. Cl. .................. 436/73; 73/61 LM; 73/DIG. 9; 356/36; 436/171; 436/174; 436/181

[58] Field of Search .............. 436/73, 127, 171, 174, 436/181; 73/864, 864.32, DIG. 8, 61 LM, DIG. 9; 356/36, 311, 313, 326

[56] References Cited

U.S. PATENT DOCUMENTS

| | | | |
|---|---|---|---|
| 3,645,628 | 2/1972 | Bojic et al. | 356/313 |
| 3,659,944 | 5/1972 | Bojic | 356/313 |
| 3,669,546 | 6/1972 | Virloget | 356/313 |
| 3,672,774 | 6/1972 | Bojic et al. | 356/313 |
| 3,963,420 | 6/1976 | Matsumoto et al. | 436/73 |
| 3,985,031 | 10/1976 | Franz | 73/DIG. 9 |
| 4,137,774 | 2/1979 | Kumbrant | 73/DIG. 9 |
| 4,151,253 | 4/1979 | Waggoner et al. | 422/102 |
| 4,154,284 | 5/1979 | Maringer | 264/8 |
| 4,533,642 | 8/1985 | Kelly | 436/73 X |

FOREIGN PATENT DOCUMENTS

| | | | |
|---|---|---|---|
| 0210349 | 11/1984 | Japan | 436/171 |
| WO85/884 | 2/1985 | PCT Int'Appl. | |
| 1116052 | 6/1968 | United Kingdom | |

Primary Examiner—Barry S. Richman
Assistant Examiner—Robert J. Hill, Jr.
Attorney, Agent, or Firm—Elroy Strickland

[57] ABSTRACT

A system is disclosed for analyzing molten metal which comprises removing a sample of metal from a source of molten metal; dissolving the sample in a solvent; and analyzing the dissolved sample to determine the contents of the molten metal. In a preferred embodiment, the sample is removed from the molten metal as solid particles in a sampling zone, conveyed in a fluid to a dissolution zone where a known quantity is dissolved for subsequent spectral analysis, and the resulting solution is then passed to a spectral analysis zone.

6 Claims, 2 Drawing Sheets

SYSTEM FOR ON-LINE MOLTEN METAL ANALYSIS

BACKGROUND OF THE INVENTION

1. Field of the Invention

This invention relates to a system for analysis of molten metal. More particularly, this invention relates to a system capable of removing a solid sample from a source of molten metal; dissolving the sample; and then analyzing the dissolved sample.

2. Description of the Prior Art

In the production of metal alloys such as, for example, an aluminum base alloy, it is desirable to determine the alloy content while the alloy is still in molten form. This, in turn, permits the addition of further alloying materials, or more base metal if the alloying metals are more concentrated than desired, while the alloy mixture is still molten.

Various methods of analyzing such molten metals are possible. In its simplest form, such analysis could comprise taking a sample from the melt and sending it out for spectral analysis. This, of course, would involve an unacceptable time lag. On the other hand, however, direct spectral analysis of the molten metal would create problems if sensitive spectrometer equipment was located in immediate proximity to a furnace containing molten metal.

Various alternative methods of analysis have been previously proposed. For example, Bojic U.S. Pat. No. 3,659,944 describes a system wherein a stream of molten metal is drawn into a spark chamber where the molten metal comes in contact with one electrode. The light or radiation generated by a spark between the molten metal and a second electrode is directed into a spectrometer to provide direct analysis of the molten metal. However, such a method involves the transport of molten metal from a furnace to the spark chamber and further results in the need to transmit the emitted spectra to the spectrometer if the spark chamber is located near the molten metal.

Virgolet U.S. Pat. No. 3,669,546 illustrates a system for analysis of molten metal wherein one electrode is placed directly into the molten metal bath and an electric arc is generated between the surface of the bath and another electrode placed adjacent the surface. The light emitted from this electric arc is then transmitted by a series of mirrors to a spectrograph where the light is analyzed to determine the content of the molten metal. Similar systems are disclosed in Bojic et al U.S. Pat. Nos. 3,645,628 and 3,672,774 wherein light is produced by generating sparks between an electrode and the surface of a crucible filled with molten metal and in contact with a second electrode. The light thus produced is directed to a spectrometer for analysis. Such systems, however, require the transmission of the emitted light to a spectral analysis apparatus spaced some distance from the furnace and thus some distance from the point of generation of the light.

British Patent Specification No. 1,116,052 shows a mechanism for analyzing molten material by passing a gas under pressure into the molten metal to produce metal particles which are then transported out of the bath to a spectrograph for analysis by feeding the particles or dust into a plasma jet. Production of metal particles from molten metal is also shown by Maringer U.S. Pat. No. 4,154,284 who teaches the production of metal particles such as metal flake by dipping a portion of a rotating wheel into a pool of molten metal. The wheel is provided with sawtooth-like serrations which pick up the molten metal as the wheel passes through the molten metal pool. As the wheel emerges from the molten metal, centrifugal force and/or contact with gases cause the now solidified metal to break off as flakes from the rotating wheel. The serrated surface of the wheel may also be cleared of any adhering metal from the molten metal pool by contacting the serrations with a brush.

Kenney International Application PCT/US84/01148, however, points out that problems such as interruption of particle flow due to clogging can occur in attempting to transport such metal powder. Instead, Kenney proposes a system for analysis of molten metal wherein an atomization die is used in connection with pressurized inert gas to form an aerosol or dispersion of solidified metal particles in the gas. This aerosol or dispersion is then delivered to an inductively coupled plasma torch which causes the particles to emit spectra characteristics of their constituent elements which may then be analyzed with a spectrometer.

SUMMARY OF THE INVENTION

It would, however, be preferable to provide a system for on-line analysis of the contents of a molten metal bath at a position remote from the bath which was not dependent on the transporting of either emitted spectra or powders and/or aerosols to the remote spectral analysis position.

It is therefore an objective of this invention to provide an improved system for the analysis of a molten metal source.

It is a further objective of this invention to provide an improved system for the analysis of a molten metal source wherein a sample of solid metal particles from the molten metal source is removed from the source, dissolved in a solvent, and then transported to a spectrometer for analysis.

These and other objectives of the invention will be apparent from the following description and accompanying drawings.

In accordance with the invention, a system is provided for analyzing molten metal which comprises removing a sample of metal from a source of molten metal; dissolving the sample in a solvent; and analyzing the dissolved sample to determine the contents of the molten metal. In a preferred embodiment, the sample is removed from the molten metal as solid particles in a sampling zone, conveyed in a fluid to a dissolution zone where a known quantity is dissolved for subsequent spectral analysis, and the resulting solution is then passed to a spectral analysis zone.

DETAILED DESCRIPTION OF THE INVENTION

Figure 1:
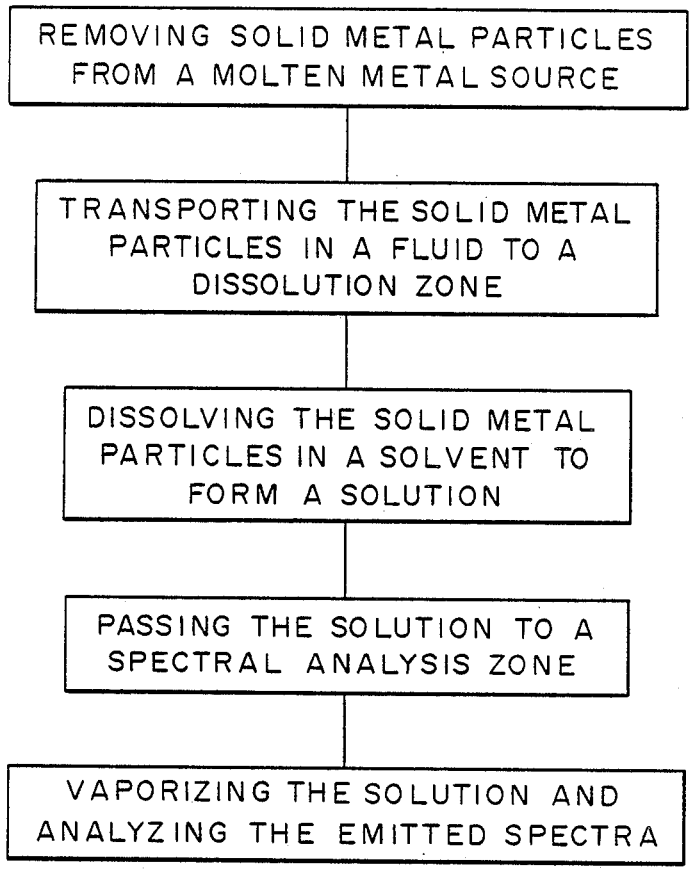
FIG. 1 is a flow sheet illustrating the system of the invention.

As depicted in the flow sheet of FIG. 1, the system of the invention provides for the collection of solid metal particles from a source of molten metal, the fluid transmission of these particles to a dissolution zone, the dissolving of the solid metal particles in a solvent, passing the solution to a spectral analysis zone, vaporization of the solution, and analysis of the emitted spectra to determine the contents of the molten metal source.

Figure 2:
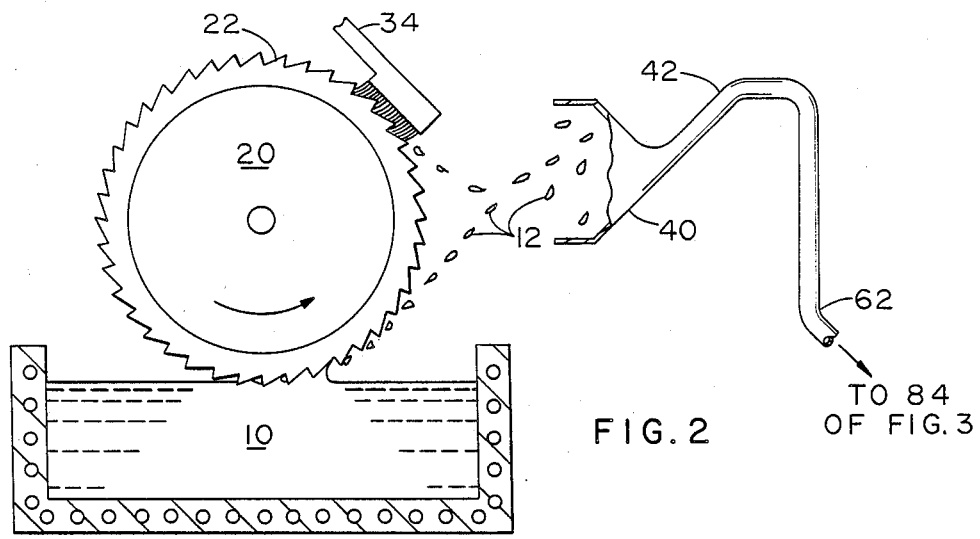
FIG. 2 is a partial cross-sectional view of a sampling zone that includes a sampling wheel.

In a preferred embodiment, as illustrated in FIG. 2, solid metal particles 12 are collected from the molten metal source 10 by partially immersing a spinning wheel 20 into the source. Wheel 20 may, for example, comprise an 11-inch diameter copper wheel, preferably with serrations or sawtooth edges 22. Wheel 20 is lowered into molten metal source 10 to a depth of, preferably, no greater than 0.5 millimeter. At the same time, wheel 20 is rotated at a speed of from about 200 rpm. As wheel 20 rotates, molten metal solidifies in the serrations 22, contracts, and is ejected from wheel 20 by centrifugal forces to be collected in hood means 40, as will be described below. A brush 34 located in the manner shown in FIG. 2 or an air jet may be used to assist in removal of metal particles from serrations 22 if desired.

Preferably, serrations 22 comprise sawtooth-shaped edges each having a leading edge of about 0.078 inch and a length of about 0.22 inch with the hypotenuse of the sawtooth forming a 20° angle with the length to thereby provide about 150 to 160 serrations on an 11-inch diameter wheel. With these dimensions, it is possible to produce metal flakes having a range of particle sizes from approximately 0.12 to 0.4 cm in length, 0.04 to 0.15 cm in width, and 0.016 to 0.020 cm thick with an approximate weight of between 0.00026 to 0.004 grams per flake.

A fairly reproducible or known amount of metal particle or flake sample can thus be collected by lowering wheel 20 into molten metal source 10 for a measured increment of time and at a known speed of rotation and then raising wheel 20 out of the pool of molten metal. Alternatively, the flakes or particles can be weighed in a weight station with an increment of sample transported to the dissolution zone only when a certain weight of sample is reached.

Figure 3:
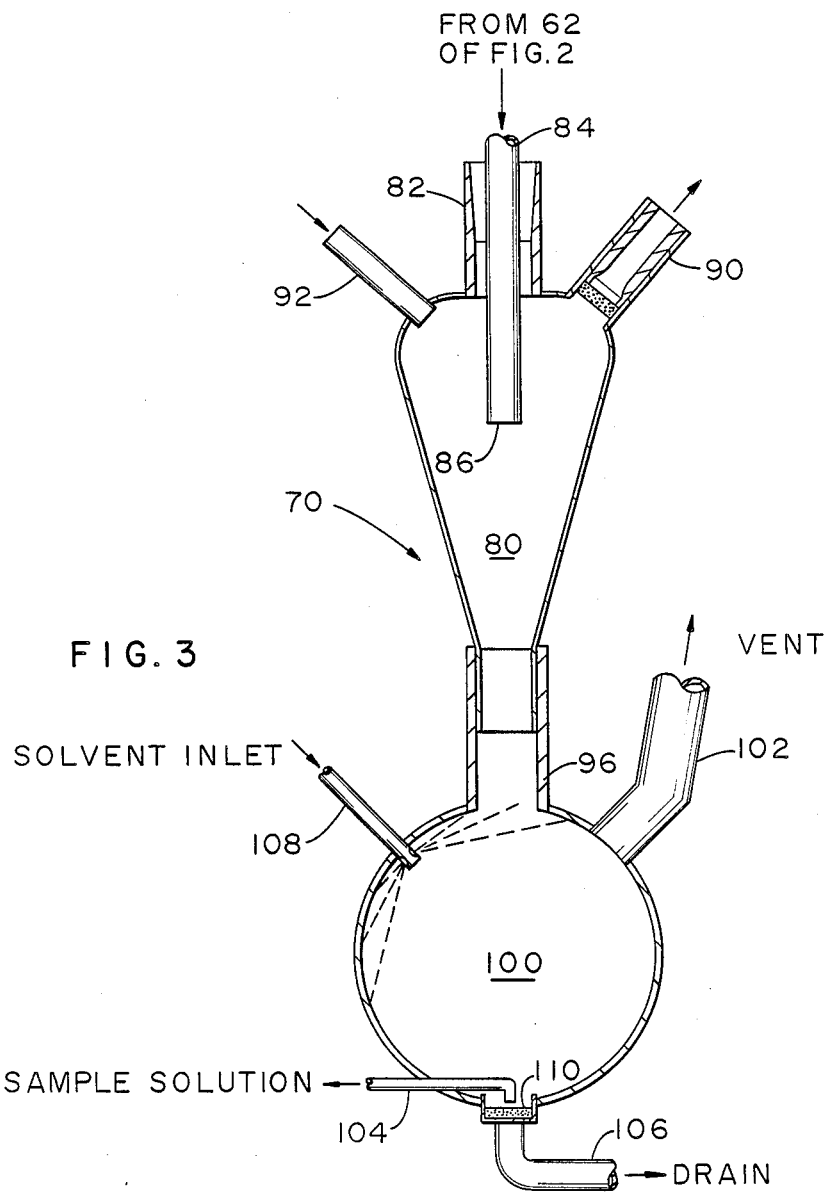
FIG. 3 is a schematic representation of a sample processing chamber, which chamber is a dissolution zone and compartment.

Turning now to FIG. 3, solid metal flakes or particles 12, as they dislodge from serrations 22 in wheel 20, are collected by hood means 40 which is positioned in the path of travel of the particles. Hood means 40 is connected, via tube or pipe 42 (FIG. 2), to a tube or pipe 62 that delivers the particles to a processing chamber 70. A vacuum is produced in 70 and in a compartment 80 of 70 by means of a blower means (not shown) attached to an exit port 90 (FIG. 3) of chamber 70. This vacuum causes metal particles to be transported from hood 40 through pipes 42 and 62 into the sample processing chamber. Tube 62 can be of substantial length to allow processing of flakes 12 at a location remote from that of their origin.

Sample processing chamber 70 includes a first compartment 80 having an inlet opening 82 connected to tube 62, which opening includes an inlet tube 84 that protrudes into compartment 80. Tube 84 terminates in an opening 86 which faces downwardly in compartment 80. The metal particles entering compartment 80 thus lose momentum and fall through compartment 80 into a dissolution chamber 100 via port 96 located below 80.

Sample processing chamber 70 includes a second, dissolution chamber 100 provided with a solvent inlet 108 through which a measured amount of solvent is admitted into chamber 100 to dissolve the metal particles entering through port 96. The solvent is dispensed in chamber 100 in such a way as to provide a washdown of the sides of dissolution vessel 100.

A lower portion of dissolution chamber 100 has a sample solution outlet 104 and a drain 106. Drain 106 contains a porous frit 110 that does not react with the solvent. Frit 110 prevents solid materials from leaving compartment 100. A vent tube 102 is shown connected to an upper side portion of compartment 100 to vent out gases that may be produced as the solid particles are dissolved. This venting is promoted by utilizing a flow of air to and through a nipple 92 during dissolution, nipple 92 being connected to an upper portion of compartment 80.

The solvent used to dissolve the metal particles preferably is a mineral acid such as a 50% HCl solution. Any other solvent capable of rapidly dissolving the metal sample may, however, be used. The term "rapidly" means the use of a solvent capable of dissolving the sample in about 30 seconds or less. For example, when a sample of aluminum flakes weighing approximately 0.1 gram is used, 10 milliliters of 50% HCl will dissolve the sample in about 10 seconds.

After the solid metal sample is dissolved, the sample solution is pumped out of dissolution compartment 100 through outlet 104 and into spectral analysis apparatus 140 (FIG. 4) in a manner described below. It should, however, be noted here that as soon as the dissolved sample leaves dissolution compartment 100 another sample may begin to be collected by again dipping wheel 20 into the molten metal to permit the collection and transport to processing chamber 70 of a new sample of solidified metal for eventual analysis. In this manner, an on-line or semi-continuous measurement of the contents of a molten metal source may be maintained.

Spectral analysis apparatus 140 may comprise any conventional spectrometer capable of vaporizing a liquid sample. Such spectral analysis equipment, conventionally known as an Inductively Coupled Emission Spectrometer, is commercially available.

Figure 4:
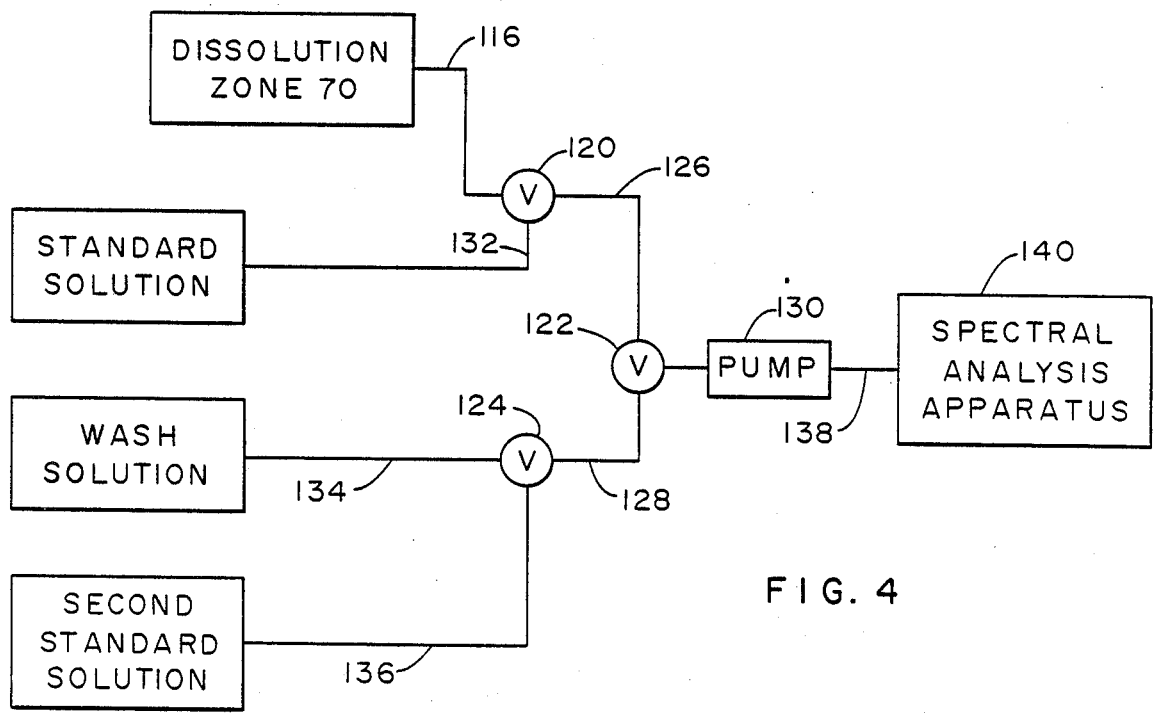
FIG. 4 is a diagramatic view of the system of the invention.

Referring now to FIG. 4, the components of which are only schematically represented, a tube 116 leads from outlet 104 (FIG. 3) to a first valve 120. Valve 120 is a three-way valve which has a second inlet 132 connecting valve 120 with a standard solution which may be used to calibrate spectral analysis apparatus 140. A tube 126 connects the outlet of valve 120 with one inlet of a second three-way valve 122. A second inlet of valve 122 is connected via tube 128 to the outlet of a third three-way valve 124. Valve 124 has an inlet 134 connected to a source of wash solution which may be pumped into spectral analysis apparatus 140 to clean the apparatus between runs. A second inlet 136 to valve 124 connects to an optional second standardized solution used to calibrate apparatus 140. Valves 120, 122, and 124 preferably are solenoid-operated valves which may be controlled by a central control unit (not shown) and which may also be used to control the remainder of the sampling apparatus, including wheel 20 (FIG. 2) and the input of solvent into dissolution chamber 100 (FIG. 3).

Connected to the outlet of valve 122 via tube 138 is a pump 130 which will pump into spectral analysis apparatus 140 whichever solution is set to pass through valves 120, 122, and 124 depending upon the settings of the valves.

The sample solution then, passes through outlet 104 (FIG. 3) and tube 116 from dissolution, chamber 100 (FIG. 3) into valve 120 and then via tube 126 into valve 122 from whence it passes through pump 130 into spectral analysis apparatus 140. The sample solution then is vaporized in spectral analysis apparatus 140 and the contents of the molten metal source are determined by comparing the emission spectra given off by a known amount of the sample to the emission spectra given off by vaporizing a known amount of a metal alloy of known alloy content.

In summary, the system of the invention provides for the analysis of a molten metal source by removing a solid sample from the molten metal source, transporting the sample to a dissolution zone in a fluidized medium, and then passing to a spectral analysis apparatus a solution containing the sample. In this manner known amounts of sample may be analyzed to determine the amount of alloying materials in the molten metal in a rapid yet accurate manner. The various zones can be controlled by a central control unit, such as a process control computer, and the zones may sequentially process different samples to thereby accelerate the overall monitoring of the content of the molten metal source.

While the invention has been described in terms of preferred embodiments, the claims appended hereto are intended to encompass all embodiments which fall within the spirit of the invention.

What is claimed is:

1. A method for analyzing molten metal in an integrated system comprising:
    (a) removing sample metal as a solid from a source of molten metal by immersing serations of a rotating disc into said source of molten metal;
    (b) transporting the sample metal by suction from the disc directly to a dissolution zone;
    (c) dissolving a measured quantity of the sample metal in a solvent in said dissolution zone to form a dissolved sample;
    (d) passing the dissolved sample from the dissolution zone to an emission spectrometer;
    (e) vaporizing said dissolved sample in the spectrometer to form a vaporized sample;
    (f) producing an emission spectra from said vaporized sample; and
    (g) comparing the emission spectra of the vaporized sample to an emission spectra of a known amount of a known alloy of the same metal as the sample metal to determine the composition of the sample metal.

2. The method of claim 1 wherein the sample metal is in the form of solidified metal particles or flakes which are formed in the serrations of the disc when the serrations are removed from the source of molten metal.

3. The method of claim 1 wherein said step (a) includes removing said sample metal from said serrations on said rotating disc by contacting said disc with means for dislodging said sample metal from said serrations on said disc.

4. The method of claim 3 wherein the dislodging means comprises a brush or an air jet.

5. A method for analyzing molten metal in an integrated system comprising:
    (a) removing sample metal as solid particles or flakes from a source of molten metal by immersing serrations of a rotating disc into said source of molten metal;
    (b) transporting said sample metal by suction from the serrations directly to a location remote from the molten metal;
    (c) rapidly dissolving a measured amount of the sample metal in a solvent at said remote location to form a sample solution;
    (d) passing the sample solution to a location for spectral analysis;
    (e) vaporizing said sample solution at said spectral analysis location to form a vaporized sample;
    (f) producing an emission spectra from said vaporized sample; and
    (g) comparing the emission spectra of the vaporized sample with an emission spectra of a known amount of a known alloy of the same metal as the sample metal to determine the composition of the sample metal.

6. A method for analyzing the content of a molten aluminum alloy source which comprises:
    (a) removing a sample of aluminum alloy from said source in a sampling zone by:
        (1) contacting said source of molten aluminum alloy with a spinning disc having serrations located along a periphery thereof by partially immersing said disc into said molten aluminum alloy source; and
        (2) collecting solidified aluminum alloy from said disc by dislodging solid aluminum alloy form said serrations as said serrations emerge from said molten aluminum alloy source to form said sample of aluminum alloy;
    (b) transporting said aluminum alloy sample by suction directly to a dissolution zone from the disc in said sampling zone;
    (c) dissolving a known amount of said aluminum alloy sample in a solvent in said dissolution zone to form a dissolved aluminum alloy sample;
    (d) directing the dissolved aluminum alloy sample to an emission spectrometer;
    (e) analyzing the dissolved aluminum alloy sample in said emission spectrometer by:
        (1) vaporizing said dissolved aluminum alloy sample to form a vaporized sample
        (2) producing an emission spectra from said vaporized sample, and
        (3) comparing the emission spectra of said vaporized sample to an emission spectra of a known amount of aluminum alloy of known alloy content.

* * * * *